United States Patent [19]

Line et al.

[11] Patent Number: 5,216,130

[45] Date of Patent: Jun. 1, 1993

[54] COMPLEX FOR IN-VIVO TARGET LOCALIZATION

[75] Inventors: Bruce R. Line; Peter B. Weber, both of Delmar, N.Y.

[73] Assignee: Albany Medical College, Albany, N.Y.

[21] Appl. No.: 525,258

[22] Filed: May 17, 1990

[51] Int. Cl.$^5$ .................. C07K 17/10; C07K 15/14; A61K 39/44; A61K 47/48

[52] U.S. Cl. .................. 530/362; 530/363; 530/391.1; 530/391.3; 530/391.5; 530/391.7; 530/391.9; 530/409; 536/51; 536/112; 424/1.1; 424/85.91; 424/450

[58] Field of Search ............... 530/362, 363, 384, 409, 530/391.1, 391.3, 391.5, 391.7, 391.9; 514/21, 59; 536/51, 112; 424/1.1, 85.91, 450

[56] References Cited

U.S. PATENT DOCUMENTS

| | | | |
|---|---|---|---|
| 4,138,383 | 2/1979 | Rembaum et al. | 524/809 |
| 4,224,198 | 9/1980 | Rembaum et al. | 525/54.1 |
| 4,413,070 | 11/1983 | Rembaum | 523/223 |
| 4,452,773 | 6/1984 | Molday | 424/1.1 |
| 4,622,322 | 11/1986 | Rembaum | 525/54.1 |
| 4,671,954 | 6/1987 | Goldberg et al. | 424/450 |
| 4,678,814 | 7/1987 | Rembaum | 522/175 |
| 4,710,525 | 12/1987 | Kraemer et al. | 523/201 |
| 4,762,915 | 8/1988 | Kung et al. | 530/405 |
| 4,829,101 | 5/1989 | Kraemer et al. | 523/201 |
| 4,861,597 | 8/1989 | Kida et al. | 424/450 |
| 4,867,973 | 9/1989 | Goers et al. | 424/85.91 |

FOREIGN PATENT DOCUMENTS 0087786 9/1983 European Pat. Off.
0357401 3/1990 European Pat. Off.
8807365 10/1988 PCT Int'l Appl.

OTHER PUBLICATIONS

Blair et al. (1983) J. Immunol. Methods 59:129-143.
Yan et al. (1988) Biotech Appl. Biochem 10(1):13-20.
Scheffel et al. (1972) J. Nucl. Med. 13: 498-503.
P. K. Gupta and C. T. Hung, *Life Sciences* 44:175-186 (1989).
E. Fattal et al., *Antimicro Agents and Chemotherapy* 33:1540-1543 (1989).
V. J. Wiebe and M. W. DeGregorio, *Rev. of Infect Dis* 10:1097-1101 (1988).
D. Liu and L. Huang, *Biochim Biophys Acta* 1022:348-354 (1990).
C.-Y. Wang and L. Huang, *Biochemistry* 28:9508-9514 (1989).

(List continued on next page.)

*Primary Examiner*—Christine M. Nucker
*Assistant Examiner*—Kay Kim
*Attorney, Agent, or Firm*—Heslin & Rothenberg

[57] ABSTRACT

To localize targets within the body (i.e., fixed intravascular antigens on emboli, neovascular endothelium, endothelium altered by regional inflammation) antibodies are linked via dextran spacer arms to rapidly cleared, Tc-99m labeled, microspheres. A micron-sized, albumin microsphere has been synthesized that is designed to enhance target surface interaction and to have a high antibody loading capacity. Stable, hydrophilic microspheres are produced from a pH dependent refolding of albumin followed by heat annealing. To couple dextran, the microspheres are derivatized with succinic anhydride and then linked via carbodiimide to succinic dihydrazide. After periodate oxidized dextran forms hydrazone linkages to the microspheres, additional dihydrazide coupled to the dextran spacer arm is used to link periodate oxidized IgG via its Fc domain carbohydrate. A milligram of the resulting 0.5-1.0 micron microspheres contains 50 to 350 ug of dextran and up to $10^5$ covalently bound IgG molecules per microsphere. Microspheres exposed to $SnCl_2$ can be labeled with 90 Mci/mg of Tc-99m. Spheres with high levels of dextran SDH clear the blood rapidly ($T_{\frac{1}{2}}=2.6-4$ min) compared to those coated with native dextran ($T_{\frac{1}{2}}=35-50$ min). These labelled albumin targeting microspheres may be used to detect a variety of sites of clinical interest using non-invasive external imaging devices and may be employed to carry therapeutic agents to these sites.

21 Claims, 3 Drawing Sheets

OTHER PUBLICATIONS

B. J. Hughes et al., *Cancer Res* 49:6214–6220 (1989).

J. Leibovici et al., *Int J Immunopharmac* 11:133–147 (1989).

S. K. Lo et al., *J. Immunology* 143:3325–3329 (1989).

D. A. A. Vignali et al., *J. Immunology* 144:4030–4037 (1990).

K. B. Hymes et al., *Blood* 75:1813–1819 (1990).

K. H. Singer et al., *J. Immunology* 144:2931–2939 (1990).

T. F. Tedder et al., *J Immunology* 144:532–540 (1990).

O. W. Blaschuk et al., *Developmental Biology* 139:227–229 (1990).

T. Nitta et al., *J. Exp Med* 170:1757–1761 (1989).

Morrison and Boyd, *Organic Chemistry, 3d Edition*, Allyn and Bacon, Inc., Boston, Mass. (1977).

*Dorland's Illustrated Medical Dictionary, 26th Edition*. W. B. Saunders Co., Philadelphia, Pa. (1981).

W. Pigman, Ed., *The Carbohydrates*, Academic Press Inc., New York, N.Y. (1957).

Hoffman, W. L. and O'Shannessy, D. J., *Journal of Immunological Methods* 112: 113–120 (1988).

Wilson, M. R. and Wotherspoon, J. S., *Journal of Immunological Methods* 107: 225–230 (1988).

Fujiwara, K., et al., *Journal of Immunological Methods*, 110: 47–53 (1988).

Schwarz, J. A. et al., *Int'l. J. of Clinical Pharmacology* 19(8): 358–367 (1981).

Rhodes, B. A., et al., *J. Nuclear Medicine* 27: 685–693 (1986).

Knight, L. C., et al., *J. Nuclear Medicine* 29: 494–502 (1988).

L. C. Knight, *Seminar in Nuclear Medicine*, vol. 20: (Jan. 1990), pp. 52–67.

Illum, L. and Jones, D. E., *Methods of Enzymology* 112: 67–84 (1983).

Gershoni, J. M., et al., *Analytical Biochemistry* 146: 59–63 (1983).

Molteni, L., *Methods of Enzymology* 112: 285–298 (1985).

Ghose, D. A., *Methods in Enzymology*, 93: 280–333 (1983).

Burger, J. J., et al. *Methods in Enzymology*, 112: 43–56 (1985).

Line, B., et al., Abstract #16363, The Society of Nuclear Medicine, 36th Annual Meeting, St. Louis, Mo., Jun. 13, 1989–Jun. 16, 1989.

COMPLEX FOR IN-VIVO TARGET LOCALIZATION

BACKGROUND OF THE INVENTION

This invention relates to radioactive microspheres that may be used to locate and irradiate specific targets within the body of an animal or human. More particularly, this invention relates to the use of a microsphere core coupled with a chemically prepared polysaccharide to which is attached a specific targeting molecule. As these spheres may also be combined with non-radioactive drugs, they can be applied to a wide variety of other uses in specific site detection with non-invasive imaging equipment (such as magnetic resonance imaging) and can be used to remove specific molecules, viruses or cells from the circulation.

DESCRIPTION OF PRIOR ART

To detect a site of interest or disease within an organism, a radioactive tracer is often employed that localizes at that site through mechanical or biochemical means. The localization or uptake of the tracer is then defined by external imaging devices such as a radionuclide gamma camera. The ability to externally detect the site of interest is dependent on a variety of factors such as amount localized, specific activity of the isotope, the attenuation of the isotope radiation and the detector efficiency. The overall detectability of a site is best summarized by the concept of a ratio of the target signal to background noise.

Mono- or polyclonal antibodies (e.g. immunoglobulin G or IgG) are being applied as carriers of radioactive isotopes to increase the localization specificity of the tracer molecule. Unfortunately there is a large amount of non-specific background in radiolabeled antibody images which decreases an observer's ability to detect sites of specific localization. To enhance target signal relative to background noise, investigators have delayed imaging from hours to days, used background subtraction and image filtering algorithms, modified the size of the antibody molecule, varied antibody dose level, altered routes of administration, added side groups to the antibody, administered secondary antibodies, and have attempted to label the antibody after localization. The problem of non-specific background is most evident with short lived tracers such as Tc-99m or when there is an acute need for clinical information. Tc-99m labelled anti-fibrin, for example, has not been efficacious in detecting pulmonary embolism.

One successful method to clear background is widely applied in liver/spleen scanning and gastro-intestinal blood loss studies. Colloidal suspensions of Tc-99m albumin microspheres are rapidly cleared by the reticulo-endothelial system (RES) leaving a small fraction of the injected dose within the vascular pool. Monoclonal antibodies can be attached to microspheres by means of absorption, direct coupling and indirect coupling via an intermediate (spacer) molecule. At their isoelectric point, IgG molecules bind firmly to hydrophobic surfaces by van der Waals-London forces. Although physical washing of the particles would appear to indicate that the antibody is strongly bound to the surface of the particle, competitive displacement of adsorbed proteins has been shown to occur. This imposes limitations on the usefulness of this technique for in vivo targeting. In fact, it has been found that in the presence of serum, the antibody-coated particles fail to bind to their target cells in vitro or to localize in vivo. The antibody can be adsorbed non-covalently onto the surface of microspheres by means of a ligand which interacts specifically with the intact or modified antibody. For such purposes, avidin-biotin and protein A have been used in coupling IgG to albumin microspheres. The latter approach may have limited usefulness in-vivo as certain subclasses of IgG bound via protein A can activate the complement system. Direct binding to microspheres may occur if functional groups capable of covalently bonding with proteins, e.g., aldehyde groups, are available on the surface of the microspheres. Proteins and other molecules, for example, can be covalently bound to latex spheres under a variety of mild conditions using water soluble carbodiimides, cyanogen bromide and glutaraldehyde. Indeed, Polystyrene latex particles have been used as immunochemical markers for scanning electron microscopy. In vivo applications of such a reagent, however, are limited because they are not biodegradable and their hydrophobic surfaces adhere non-specifically to many tissues and molecules. Microspheres polymerized from natural materials such as albumin and gelatin contain surface amino and carboxyl groups that can be used to attach antibody molecules. Coupling sites may also be introduced, i.e., free aldehyde groups can be generated by cross-linking albumin with glutaraldehyde. Unfortunately, direct linkage of antibody to microsphere surfaces may compromise the active site or block it through steric effects.

Studies of therapeutic drugs conjugated to antibodies via dextran spacers have shown increased drug stability to light, temperature, hydrolysis and chemical agents. Dextran has also been shown to improve the drug hydrophilicity, thereby reducing nonspecific in-vivo interactions which are generally hydrophobic. The dextrans used clinically as blood volume expanders are biosynthetic polymers consisting of linear chains of glucose in a 1:6 linkage. Dextran conjugates are temporarily retained by tissues of the reticuloendothelial system and accumulate mostly in the liver where they are metabolized by dextranases.

There have been studies that evaluate optimal conditions for coupling monoclonal antibodies to small (580 Å) unilamellar liposomes. These authors were successful in coupling from 1 to 10 antibody molecules per liposome with at least 80% of liposomes carrying nondenatured antibody. The coupling reagent provided a six carbon spacer between the coupled antibody and the liposome. Measurements of liposome size and calculations based on moles of antibody bound per mole of lipid indicate that one molecule of coupled antibody was sufficient to bind liposomes to *Staphylococcus aureus*, or to target cells in vitro. This is in contrast to other reports, in which as many as 16 molecules of antibody coupled directly to palmitic acid in liposomes were insufficient to bind the liposomes to target cells. The latter result was felt to be consistent with steric hindrance based on proximity of the coupled antibody molecules to the liposome membrane.

Albumin microspheres have been labelled with Tc-99m in preparations of colloids for liver and lung scanning. The most common method of labelling uses stannous chloride but a variety of techniques have been employed. However, labelling of microspheres linked to antibodies has, it is believed, not been utilized. The labelling of microspheres with technetium is highly dependent on the microsphere composition and is made difficult by the tendency of technetium and tin to form into colloidal suspensions at body pH. This confounds the labelling of the microspheres.

SUMMARY OF THE INVENTION

The invention features a macro-molecular complex constructed from a unique formulation of a microsphere central core together with a long spacer arm that is chemically prepared to attach to a specific targeting molecule. This design provides a favorable signal to noise ratio due to the contrast between the high targeted sphere activity and the low, RES cleared, background. The macro-molecular complex described in this disclosure will hereafter be referred to as the complex.

The complex comprises a supporting central core, a polysaccharide spacer arm connected to the central core, and a specific targeting molecule that is attached to the spacer arm. The central core is typically heat denatured albumin and the specific targeting molecule is typically an antibody. A polysaccharide such as dextran can be used as the connecting arm. The complex resulting from the preferred embodiment is essentially a huge multi-valent antibody with hundreds of thousands of specific targeting molecules and a high tracer activity. The central core restricts the antibody-tracer complex to the intravascular space where non-specific activity can be cleared. However, the size of the complex does not restrict its access to the endothelium that is altered by vascular disease (clots, plaque), or which contains neovascular antigens or the molecular signals controlling cell traffic in regional inflammation.

The complex is produced by forming the central core from a material that is appropriate for in-vivo use, by linking the core to a spacer arm appropriate for in-vivo use that is sufficiently long to provide high cross section for specific targeting molecule attachment, and by connecting a specific targeting molecule to this arm. A symmetric hydrazide may also be used for coupling the spacer arm to both the central core and the specific targeting molecule. The complex may be labelled with a radio-isotope to allow its in-vivo localization.

The complex is injected into the blood to allow external identification (through the use of an imaging device or detector) of sites that are located by the specific targeting molecules attached to the complex. The complex provides a means for achieving high target signal to background noise ratio and hence improved target detection. This results from a combination of high complex tracer loading and low background noise due to prompt clearance of non-targeted complex from the blood. Alternatively, the complex may be used to clear the blood of targets such as antibodies, drugs, viruses or cells that become attached to the specific targeting molecules.

DESCRIPTION OF THE PREFERRED EMBODIMENTS

In its preferred embodiments, the microsphere complex is novel in its application to external imaging because it can be efficiently coupled with glycoproteins (antibodies) and labelled with large quantities of Tc-99m to provide it with a highly detectable signal at a target site. Furthermore, the complex can be cleared from the circulation with a rapid but controllable rate to allow a low background noise. This original combination is effective in producing a high signal to background noise ratio that is important in external detection, and which is very difficult to achieve with previous antibody mediated tracer localization technology.

Preparation of Central Core

Figure 1:
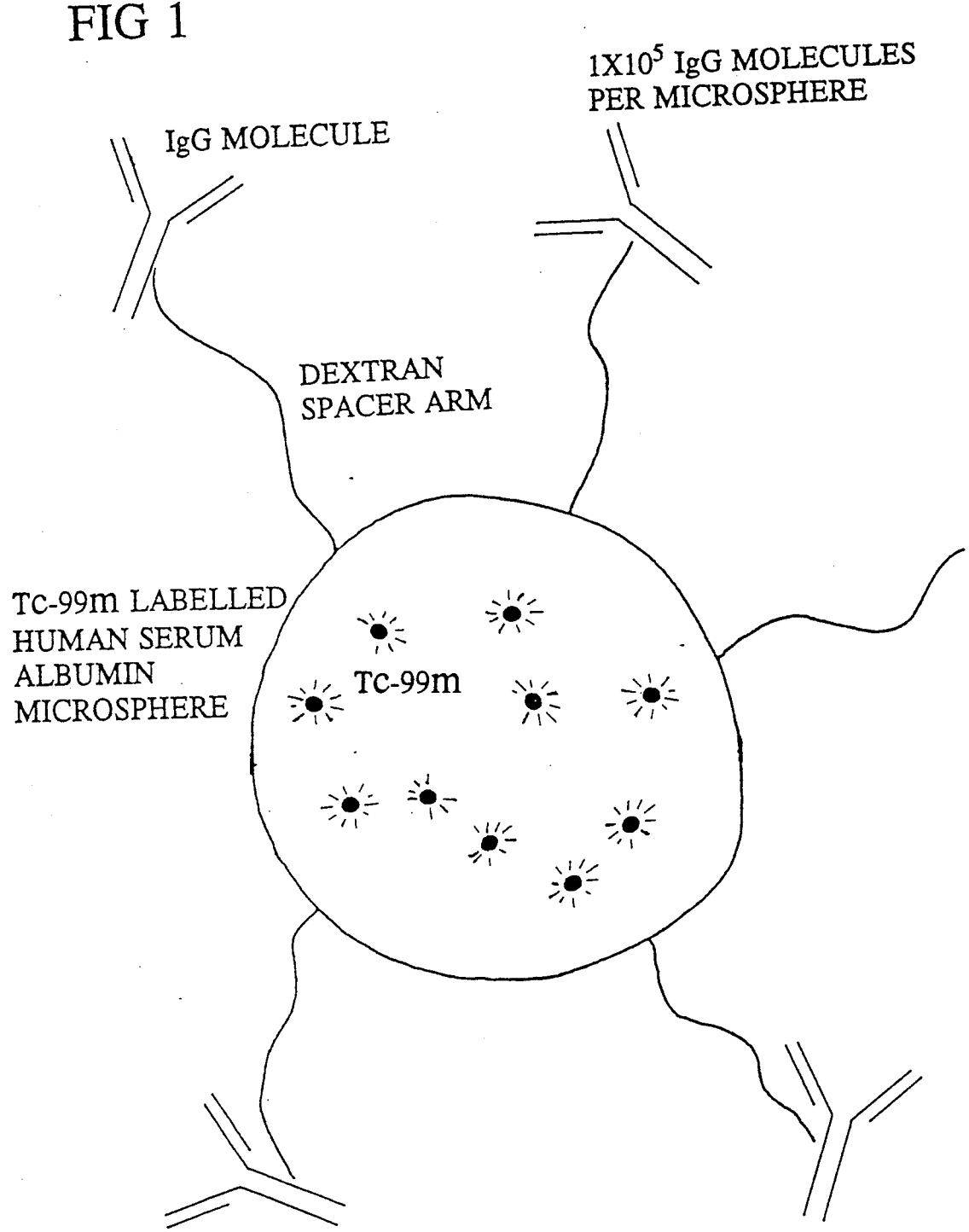
FIG. 1 is a diagrammatic representation of a targeting microsphere complex.

The central core is typically 10000 Å in diameter (see FIG. 1) but may vary in size depending on the preparative procedure. The micron sized central core has been synthesized to withstand the chemical manipulations necessary to attach monoclonal antibodies (see FIG. 1). The albumin colloids used for liver scanning are dissolved by high or low pH, ultrasonication or reductions in stabilizing quantities of free albumin. To achieve a better foundation for covalent attachment of antibodies, microspheres are formed from albumin in the absence of wetting agents and are heat annealed. This treatment provides relatively uniform, stable spheres that are easily labelled with Tc-99m (see FIG. 1).

Microspheres are produced using simple equipment. Mild heat and elevated pH serve to uncoil the protein such that subsequent cooling and reduced alkalinity causes refolding into globular clumps. The pH of the solution during the refolding process largely determines the final size of the spheres. Spheres between 10 and 20 mu are formed with neutral pH solutions while larger spheres result from mildly acidic solutions (pH >5.0). In the preferred embodiment, at about pH 6.2 the solution is moderately opalescent and particulates are barely visible microscopically (45x). At this point the solution is flash heated in a 85° C. water bath. A similar procedure described by Taplin [J Nucl Med 1964, 5:259-275] does not include a flash reheating step. Heating the microspheres appears to strongly stabilize them, for without this step, the particulates are poorly resistant to high (>11) or low (<2) pH, ultrasonication and chemical surface modification.

In the preferred embodiment, a 1% solution of essentially fatty acid-free albumin (Sigma A-6289) is prepared by dissolving 2 grams of albumin in doubly distilled deionized water. Tracer quantities of desalted (PD-10 Sephadex column, Pharmacia) I-125 Human serum albumin (Mallinckrodt Diagnostic Products) are added and the solution is raised to pH 10 with 1M NaOH. The mixture is heated at 80° C. for 20 minutes and cooled on ice to room temperature. After the solution pH is neutralized with 0.1M HCl, 0.05M HCl is added drop wise with continuous stirring. As the solution approaches pH 6.2, one half ml aliquots are swirled in small glass test tubes in a 85° C. water bath and are examined on a hemocytometer. When particles of 0.5-1.0 micron are evident microscopically (45x), the solution is passed through 1 meter of intravenous tubing (Baxter 2C5545s) that is immersed in the water bath (30 second transit time). The particulates are centrifuged at 100 rcf for 5 minutes to remove large aggregates. Protein mass incorporated into microspheres is determined by measurements of activity recovered in samples spun at 4300 rcf. Average size is measured from electron micrographs. Typical yields vary between 40 and 70% protein recovery in microspheres ranging from 0.5 to 1 micron in diameter. After large aggregates are removed, the microsphere solution is maintained at pH 7.5 with 2 M NaOH while 10 grams of finely powdered succinic anhydride (Sigma S-7676) are added in small quantities. To remove reaction products, the particulates are titrated to pH 4.0, and washed 4 times by 4300 rcf centrifugation and resuspension in distilled water using low wattage ultrasonication (3M Ultrasonic bath).

Production of Polysaccharide Derivatized Microspheres Using Dextran

As it is desired to give the antibody a high degree of rotational freedom and reduced steric hindrance, a polysaccharide (e.g. dextran) spacer arm (see FIG. 1) has been chosen to link antibodies to the microspheres. Polysaccharides are made up of many, e.g. hundreds or even thousands, of monosaccharide units per molecule. Typical polysaccharides have 5 or more monosaccharide units per molecule. In the preferred embodiment, dextran of molecular weight up to four million (or about 24,000 glucose units) provides an uncharged, hydrophilic, relatively inert, linear arm for which mild procedures can be used in antibody coupling. The polysaccharide linked to the surface of the albumin core allows a very high complex targeting molecule loading capacity which far exceeds that previously reported. It most likely provides a very high cross-section for molecular attachment that shorter spacer arms or direct microsphere coupling is not capable of providing. Based on a dextran loading of 200 ug dextran per milligram of microspheres and 2 billion microspheres of 1 micron diameter per milligram, there is a potential for over 6 million attachment sites per microsphere.

In the preferred procedure, the polysaccharide molecule is oxidized to provide the aldehyde groups that will subsequently undergo Schiff base formation with microsphere hydrazide groups. Sodium periodate which attacks vicinal hydroxyls within the glucose rings of dextran, for example, generates these aldehyde attachment points. Assuming the periodate attack is random relative to the glucose rings in dextran molecules, a combinatoral analysis predicts a distribution of oxidations wherein the probability P of n oxidations on a given molecule is expressed as:

$$P(n) = (e^{-u} * u^n) / n!$$

where u is the mean number of oxidized molecules per dextran. A mean oxidation of 1, for example, produces the largest amount of dextran molecules with a single chain oxidation although a relatively large fraction of molecules remain unoxidized.

Suitable conditions for dextran attachment are determined from experiments wherein the dextran concentration, reaction time and pH are varied. Four and ten millimolar dextran solutions are combined with hydrazide derived spheres after the dextran is oxidized with equimolar quantities of sodium periodate. The reactions are carried out for 90 minutes in 0.05M NaOAc, pH 4.0 at room temperature. Dextran loading is found to be initially rapid but tends to level off after twenty minutes. The nearly proportional relationship between dextran concentration and microsphere loading suggested by these results is further evaluated at various reaction hydrogen ion concentrations. These preparations are reacted for 1 hour, again using dextran that is oxidized with equimolar amounts of periodate. Dextran loading appears nearly proportional to dextran concentration at pH 6, but tends to plateau as the solution pH drops to 4.0. This pH dependence is also evident with increasing dextran oxidation (i.e., as molar ratio of periodate to dextran increases from 1 to 4).

The polysaccharide coat provides a substrate for attaching groups that determine the rate of particulate clearance by the reticuloendothelial system. It is possible to vary the rate of particulate clearance by changing type or the amount of polysaccharide on the sphere surface or by adding to the polysaccharide coat other substances that modify clearance. To study the effect of different surface coats on the blood residence time of microspheres, experiments were carried out in rabbits using native microspheres, commercially available albumin colloid and microspheres coated with both dextran and dihydrazide groups. Images obtained with all particulate preparations show clearance by the reticuloendothelial system. The native spheres, albumin colloid and dihydrazide covered spheres demonstrate a rapid and comparable clearance with a disappearance half time of between 2.5 and 4 minutes. The dextran coated spheres show a longer clearance half-life of between 35 and 50 minutes. The optimum rate of clearance will depend on the kinetics of complex localization at the target site. Although it is desirable to clear background prior to imaging, very rapid clearance may result in an antibody-antigen interaction time that is too short to provide a detectable signal at the target site.

The preparation of the polysaccharide derived microsphere complex can be effected by several methods.

METHOD 1

Derivatization by Sequential Reactions Involving the Microsphere Core

Figure 2A:
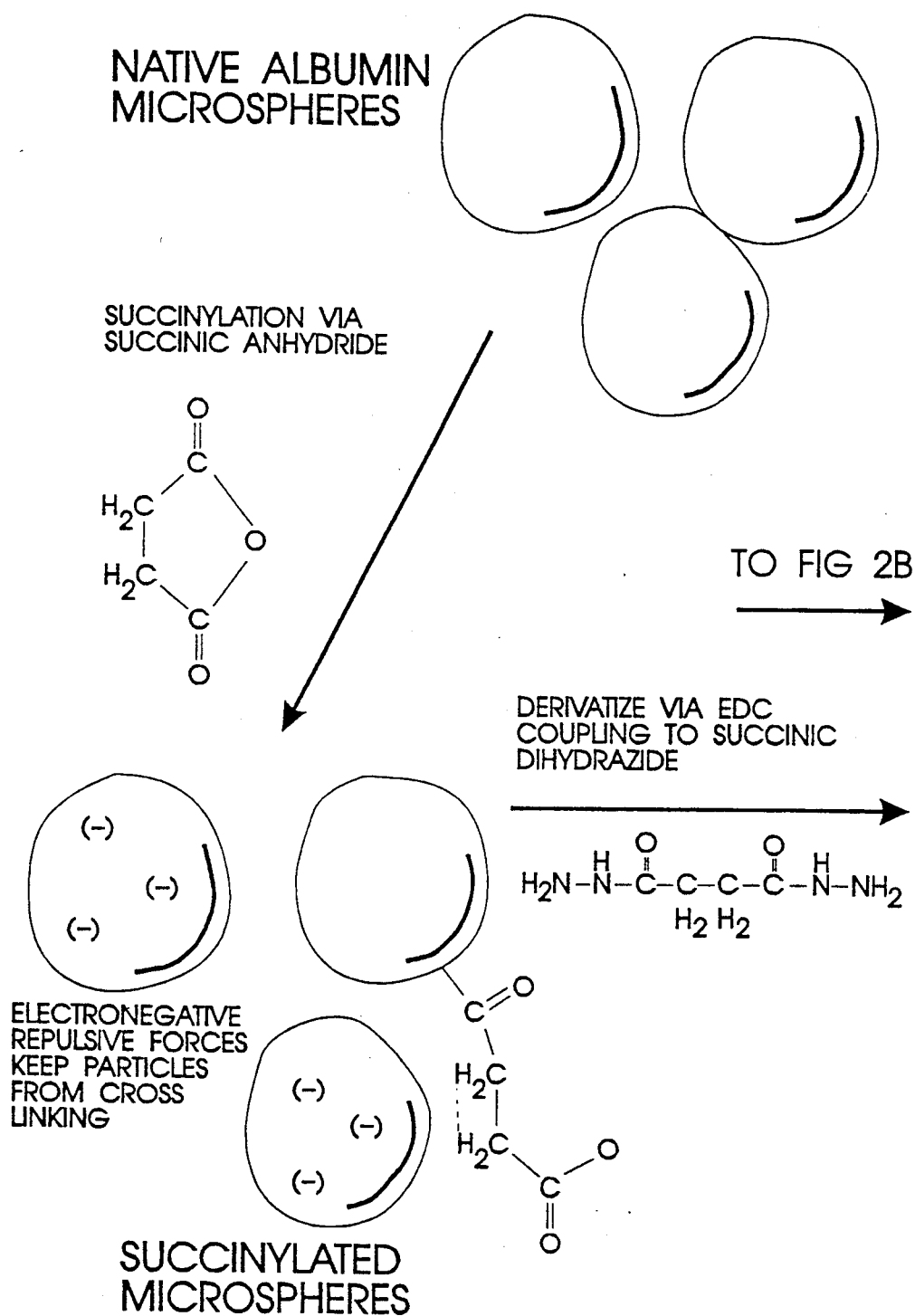
FIG. 2 is a schematic of the process linking albumin microspheres to whole immunoglobulin molecules. The surface of the spheres is first derivatized using succinic anhydride to provide a linkage site for the dextran spacer arm and to keep the particulates from cross-linking during subsequent modification. Succinic dihydrazide is used to couple the dextran to the sphere and the antibody.
Figure 2B:
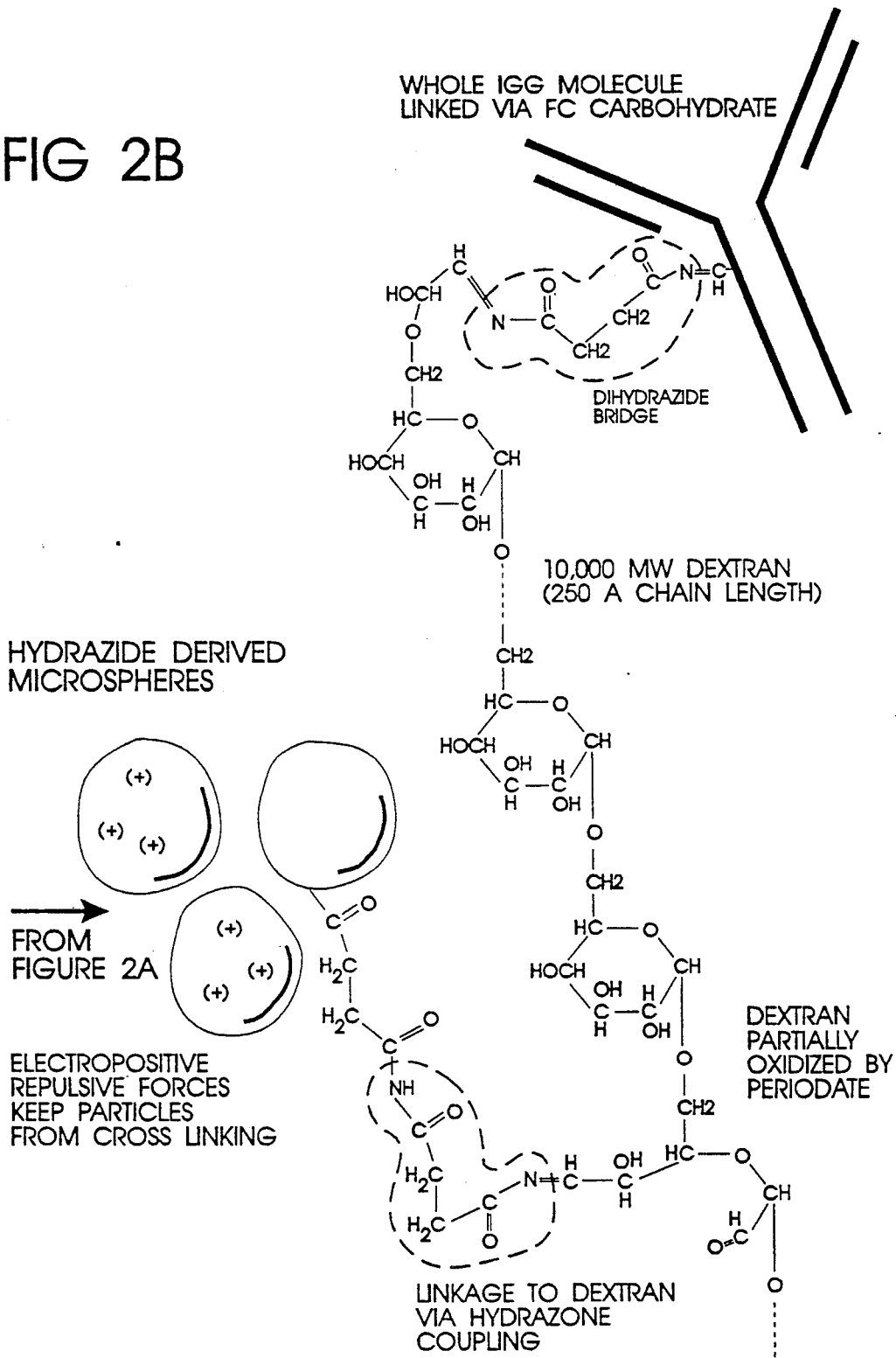

Dextran is coupled after microsphere treatment with succinic anhydride and succinic dihydrazide (see FIG. 2). Treatment with succinic anhydride provides a uniform chemical interface of carboxyl endgroups, and a highly electronegative surface (see FIG. 2) that maintains microsphere separation during linkage to dihydrazide. Once attached, the dihydrazide endgroups convert the spheres to an electropositive state (see FIG. 2) which again prevents particulate cross-linking. To couple antibody to the dextran spacer arm, a succinic dihydrazide bridge is attached to the glucitol at the reducing end of the dextran molecule (see FIG. 2). The borohydride used to "stabilize" the microsphere-to-dextran Schiff base bond also reduces the terminal glucose ring on dextran to glucitol allowing it to be rapidly oxidized by sodium periodate. The feasibility of this approach is demonstrated by the oxidation kinetics of three test dextran solutions. The first is reacted with an equimolar quantity of sodium periodate, then reduced with borohydride. The second is just reduced with borohydride and the third serves as a control. All three solutions are treated with equimolar quantities of periodate and the absorbance of the reaction mixture is measured for 20 minutes at 250 nm. This study shows a rapid fall of periodate absorbance for both reduced dextran preparations relative to control. This confirms that oxidation of terminal open chain glucitols is favored relative to intact rings, and implies that prior oxidation of the dextran does not destroy this potential linkage site. Coupling a dihydrazide molecule to the reducing end of the dextran chain provides an average spacer arm of approximately 125 Å, i.e. half of the native dextran chain length. Procedure: The succinylated microspheres are suspended in 0.5M succinic acid dihydrazide (SDH, Alfa Products 16200) and are reacted at pH 5.0 with 0.1M of EDC (1-ethyl-3-(3-dimethyl-aminopropyl) carbodiimide, Sigma E-7750) for 2 hours at room temperature. The hydrazide derivatized microspheres are washed 4 times and stored at 4° C. Dextran (MW 9400, Sigma D-9260) is prepared in a 20 mM solution and added to an equal volume of 20 mM sodium meta-periodate (Sigma S-1878). This is reacted in the dark at room temperature, pH 4.0, for 30 minutes. The reactants are dialyzed to remove residual periodate and iodate by-products before combining with the hydrazide microspheres. Dextran is coupled to microspheres via Schiff base bonds formed during a one hour reaction at pH 4.0. These bonds are stabilized with 50 mM sodium borohydride (Sigma S-9125, pH 9.0, in borate buffer) for 1 hour at room temperature. Dextran loading per mg microspheres is determined by the phenol-sulfuric acid colorimetric reaction. Dextran coupled microspheres are suspended in equal volumes of 20 mM native dextran and sodium periodate buffered to pH 4.0 with 0.05M sodium acetate (NaOAc). The particulates are immediately washed 4 times in distilled water and resuspended for 2 hours in 100 mM SDH, pH 6.0. The Schiff bases formed between the dextran and SDH are reduced with 50 mM sodium borohydride for 1 hour at pH 9-10. The product is washed 4 times and stored at 4° C.

METHOD 2

Microsphere Derivatization by Coupling Dextran-Succinic Dihydrazide Construct Dextran is first reduced to produce terminal glucitols with sodium borohydride and then oxidized to create a terminal aldehyde and several other reactive aldehydes at random sites along the polysaccharide backbone. The iodate reaction products are removed by dialysis and succinic dihydrazide is reacted with the dextran chain. Schiff bases formed between SDH and dextran aldehyde functions are reduced with sodium borohydride and the reaction product is exhaustively dialyzed.

Procedure: 10 grams of dextran and 3 ml of 1M NaHCO$_3$ buffer are diluted to 30 ml with distilled, deionized water and 480 mg of NaBH4 are added. The pH is maintained at 9.5 with 1M NaOH over a 3 hour reaction period, following which the pH is reduced to 4.5 using 2M HCl. A three molar ratio of NaIO4 (680 mg) was added and reacted for 30 minutes at room temperature in the dark. The pH was maintained at 4.5 during the reaction and the reactants are dialyzed to remove iodate byproducts. The dialysate was combined with 25 grams of succinic dihydrazide that had been recrystallized in the cold after solution in 20 cc of water and 4300 rcf centrifugation to remove solid impurities. The reactants were adjusted to pH 5.5 with 0.1M NaOH and the Schiff base coupling reaction was allowed to proceed overnight at room temperature. The pH of the solution was then raised to 9.5 with 2M NaOH and 240 mg of NaBH4 was added to stabilize the SDH—dextran bonds. The resulting product is exhaustively dialyzed against distilled water using 2,4,6-trinitrobenzenesulfonic acid [Fields, Meth. Enzymol, 25,464 (1972)] to check for free SDH and determine the molar ratio of SDH to dextran. Typically, 4-6 moles of SDH are found per mole of dextran.

To couple the SDH derivatized dextran to succinylated microspheres, a final concentration of 40 mM EDC is achieved in a solution containing 5 mg/ml microspheres and 50 mg/ml of SDH-dextran. The reaction is carried out at pH 5 for two hours at room temperature. Typical dextran loading determined by the phenol-sulfuric acid test and microsphere I-125 counts is 300-350 ug dextran per mg of microspheres.

METHOD 3

Microsphere Derivatization Using Hydrazinodextran

Sodium borohydride reduced dextrans are reacted with p-toluenesulfonyl chloride. The product, mainly 6-O-p-tolylsufonyldextran is converted into the 6-hydrazino-6-deoxydextran by refluxing with hydrazine and the product is coupled to the carboxylated microspheres. As dextran is mainly a 1-6 glycan, the nitrogen functions are mainly located at the original terminal primary hydroxyls; for instance C1 of the reducing end glucitol and C6 of the non-reducing end glucopyranoside. The periodate oxidized IgG is then directly coupled to the terminal hydrazines via reductive amination with sodium cyanoborohydride. This approach reduces the number of coupling steps considerably. The hydrazinodextrans are prepared in bulk and characterized in respect to molecular weight and substitution. Procedure: Dextran (10,000 MW) 32.4 g is dissolved in 200 ml of 95% pyridine and water is removed at 60° C. by rotary evaporation. To the swollen dextran in 2 hours is added 85 grams of p-toluenesulfonyl chloride and the mixture kept for 24 hours at 25° C. After addition of 100 grams of ice and 100 ml of methanol, the mixture is agitated in a blender and the powder is washed with 80% methanol and dried. Twenty-five grams of this material is refluxed for 7 days with 35 ml of anhydrous hydrazine under nitrogen. Excess hydrazine is removed in vacuo and the residue dissolved in 5% acetic acid, dialyzed against water, and lyophilized. This material is analyzed for sugar content and hydrazinosugars by ion exchange chromatography. To calibrate against known compounds the hydrazinodextran is reduced with excess Raney-nickel (1 g/g/10 ml water of hydrazinodextran) for 24 hours. After heating to 100° C., the catalyst is removed by filtration and the product dialyzed and lyophilized. Hydrolysis and analysis for constituents gives a high ratio of glucose: 6-amino-6-deoxyglucose : 1-amino-1-deoxy-D-glucitol (D-glucamine) [50:1]. Coupling of the hydrazinodextran to the succinylated microsphere would be accomplished using EDC as described under method 2 above.

Preparation of Antibody and Coupling Procedure

Although target localization rates are a function of many physiologic and antibody factors, antibody uptake at intravascular sites should be significantly faster than at extravascular sites. For example, an extracorporeal perfusion study of a fibrin specific antibody demonstrated 70 percent of maximal antibody localization within 10 minutes of systemic circulation. Despite the fact that individual antibody molecules may dissociate from a target, the complex is less likely to uncouple due to its multivalency. It can be expected that the strength of the binding should grow rapidly after initial target interaction as the number of antibody-antigen combinations increases at the target surface.

To provide a bridge between the dextran derived microsphere and IgG, SDH is coupled initially as hydrazone and then after borohydride reduction as hydrazine linkages to the end of the dextran chain. The principle of the preferred method for antibody-complex coupling is based on the reactivity of aldehyde groups generated at the $C_H2$ region sugar moiety of the IgG molecule. In contrast to immunoglobulin amino acid residues (usually used to couple other molecules to IgG), the carbohydrate prosthetic groups furnish linkage sites that do not usually interfere with antibody activity. Because of their solubility, hydrophilicity, and bulk, oligosaccharides are found on the exterior of the protein and are thus accessible. Favorable conditions for treatment of IgG with periodate and subsequent condensation of the oxidized product with amino compounds have been established. The preferred method employs sodium meta-periodate oxidation of carbohydrate cis-vicinal hydroxyl groups. The resulting aldehyde functions react at pH 4-6 with hydrazide to form Schiff bases. This reaction is quite favorable since carbonyl groups react with hydrazides more completely than with primary amines. The conditions described in the embodiments preserved more than 90% of antibody activity.

Anti-glucose oxidase (AJG-0122 Accurate Chemical and Scientific Corporation) and anti-sulfanilic acid are used in the antibody studies. Tracer quantities of antibody labeled with I-131 (IODO-GEN, Pierce 28600) are employed to follow preparative steps and antibody coupling yields. Prior to each use, the labeled antibody is desalted through Sephadex (PD-10 column). Antibody is exchanged into 0.1M sodium acetate buffer, pH 4.0, and combined with 20 mM sodium periodate for 30 minutes in the dark at room temperature. The oxidized antibody is separated from periodate and reaction byproducts by desalting through a PD-10 column equilibrated with 0.1M sodium acetate, pH 4.0. Antibody bioreactivity after oxidation is checked by ELISA assay. The oxidized antibody is coupled to microspheres in 0.1M sodium acetate buffer, pH 5.5, overnight, and then stabilized with 50 mM borohydride for 1 hour. Preservation of antibody function is checked by precipitation of washed anti-sulfanilic acid coupled complex with native microspheres derivatized with the diazonium salt of sulfanilic acid.

Tc-99m Labelling of Complex

The protein core and polysaccharide coat are the primary sites for Tc-99m tracer labelling. Although the site of Tc-99m attachment is unclear, the mass of albumin and dextran is relatively high in comparison to the antibody and provides a greater sink for Tc-99m labelling. The microsphere complex can carry a large amount of tracer relative to a single antibody, which on a uCi/ug IgG basis, can easily exceed a factor of 10. Given the potential for rapid blood clearance, the microsphere complex should allow target imaging at an early enough time that a slow loss of Tc-99m from the microsphere in vivo will not be clinically evident.

The complex may be labelled in various manners depending on the radioisotope chosen. Labelling may be through an association with components of the complex directly or via linker molecules attached to the complex (e.g. a chelating molecule coupled to dextran hydrazide). Isotopes commonly available for this purpose include, for example, Tc-99m, In-111, and I-131. In the preferred embodiment, Tc-99m is used to label the complex by one of the two methods defined below:

METHOD 1

Stannous Chloride in Acidic Solution and Washed Complex

Low pH (<2.5) is required to dissolve $SnCl_2$ so that it can subsequently interact with the albumin microspheres. At pH levels below 2.5 glycosidic bonds may be hydrolyzed and antibodies can be damaged, hence complex microspheres are maintained just above this pH, soaked in stannous chloride solution to allow adsorption, washed of free tin and then labelled via tin mediated reduction of Tc-99m. In tests without the presence of complex, at the final pH of approximately 2.5 and a tin chloride concentration of 1 mg/ml, no colloid formation is detected after 4300 rcf centrifugation. The washing removes free stannous ions that otherwise would be available to form colloid as the pH is raised back to the physiologic range. Even after multiple washes, the amount of tin associated with the spheres appears sufficient to reduce nearly all of the added pertechnetate.

Procedure: A nitrogen purged solution of stannous chloride 1 mg/ml is prepared by dissolving $SnCl_2$ in 12N HCl and diluting it with distilled water, adjusting the pH to 2. 200 ul of this is added for each ml of complex microspheres (1-10 mg/ml) buffered in citric acid to pH 3. The particulates are allowed to incubate in this solution for one minute prior to centrifugation and are washed with sodium acetate buffer 0.1M, pH 3 and then pH 5.5. Particulates may be stored at this point or immediately combined with Tc-99m. Labeling efficiency studies using Tc-99m are performed by comparing pellet to supernatant counts after incubation for 5 minutes and 4300 rcf centrifugation. Greater than 90% labelling efficiencies are achieved with up to 90 mCi of Tc-99m per mg of microspheres.

METHOD 2

Low Concentration Stannous Chloride Without Wash

When low concentrations of stannous chloride are used it is not necessary to wash the complex to avoid tin colloid formation. It appears that even in mildly acidic solutions colloid is not produced if a sufficient quantity of albumin is present.

Procedure: A nitrogen purged solution of stannous chloride 200 ug/ml is prepared by dissolving $SnCl_2$ in 12 N HCl, diluting it with distilled water and adjusting the pH to 1.8. 100 ul of this is added for each mg of complex microspheres (1-10 mg/ml) buffered in nitrogen purged 0.5M sodium acetate, pH 4. The solution may be lyophilized or labelled immediately with Tc-99m (200 ul). Labelling efficiencies greater than 96% are routinely achieved.

Examples of applied practice follow:

EXAMPLE 1

Fixed Target Detection 20 mg whole anti-fibrin antibody is desalted through Sephadex (PD-10 column). Antibody is exchanged into 0.1M sodium acetate buffer, pH 4.0, and combined with 20 mM sodium periodate for 30 minutes in the dark at room temperature. The oxidized antibody is separated from periodate and reaction byproducts by desalting through a PD-10 column equilibrated with 0.1M sodium acetate, pH 4.0. Oxidized antibody is coupled to the complex in 0.1M sodium acetate buffer, pH 5.5, overnight, and then stabilized with 50 mM borohydride for 1 hour. The complex is washed in 0.1M acetate buffer, pH 4.5, made isotonic with 0.9% NaCl and combined with 20 ug/mg complex of $SnCl_2$. The final solution is lyophilized. Prior to use 1 ml of Tc-99m (5–10 mCi) is added in $N_2$ purged isotonic saline and the solution is administered intravenously. Fifteen to 30 minutes later, gamma camera images are obtained to identify sites of fibrin deposition as appropriate to a patient's presumed condition. For example, these images could be employed to locate venous thrombi, pulmonary emboli or fibrin deposition in association with arterial plaques as may be present in the coronary arteries in patients with acute angina. Instead of anti-fibrin, other antibodies could be employed to identify sites of fixed endothelial antigens such as found in association with neovascular endothelium or endothelium containing inflammation-associated antigens.

EXAMPLE 2

Clearance of Target Antigen 20 mg whole anti-murine antibody is desalted through Sephadex (PD-10 column). Antibody is exchanged into 0.1M sodium acetate buffer, pH 4.0, and combined with 20 mM sodium periodate for 30 minutes in the dark at room temperature. The oxidized antibody is separated from periodate and reaction byproducts by desalting through a PD-10 column equilibrated with 0.1M sodium acetate, pH 4.0. Oxidized antibody is coupled to complex in 0.1M sodium acetate buffer, pH 5.5, overnight, and then stabilized with 50 mM borohydride for 1 hour. The complex is washed in 0.1M acetate buffer, pH 4.5, made isotonic with 0.9% NaCl and lyophilized. A patient receives a Tc-99m or In-111 labelled murine antibody as appropriate to detect a tumor (e.g. 1 mg Tc-99m NR-Lu-10, NeoRx Corp, small cell or non-small cell carcinoma) and 14–17 hours thereafter, 5 mg of anti-murine antibody coupled complex is reconstituted in isotonic saline and administered intravenously to combine with any remaining intravascular Tc-99m murine antibody. The non-specific blood pool activity remaining on freely circulating murine antibody is thereby cleared with the complex by the patient's reticulo-endothelial system allowing greater detection efficiency of the specifically localized (tumor associated) extravascular antibody. Through the clearance of non-specific antibody, the background activity is reduced and the target signal to noise ratio is enhanced.

EXAMPLE 3

Clearance of Target Drug, Virus or Cell

As in example 2, complex is prepared in lyophilized form containing a non-radiolabelled antibody specific for a toxin, drug (overdose), virus or undesired cellular element. This is administered to a patient to clear the target from the circulation to the reticuloendothelial system (primarily the liver) where it is inactivated or phagocytized and destroyed.

Although the specific methods of production and utilization of the invention have been described as preferred embodiments herein, it is apparent that the invention may be constructed and utilized in a variety of manners and means not specifically mentioned herein. Any such modifications to these embodiments are intended to be within the spirit and scope of the invention as defined by the following claims.

I claim:

1. A macro-molecular complex for target localization comprising:
   a bio-compatible, in-vivo circulatable central core having a surface thereof;
   a polysaccharide spacer arm coupled to the central core; and
   a specific targeting molecule coupled to the spacer arm; wherein the polysaccharide spacer arm comprises five monosaccharides to twenty-four thousand monosaccharides and wherein said polysaccharide is coupled to the surface of said central core such that said polysaccharide is not incorporated into said central core, said polysaccharide thereby being oriented so that the specific targeting molecule has translational freedom and reduced steric hindrance when coupled to the polysaccharide spacer arm.

2. The macro-molecular complex for target localization of claim 1 wherein the central core comprises albumin.

3. The macro-molecular complex for target localization of claim 1 wherein the polysaccharide spacer arm comprises dextran.

4. The macro-molecular complex for target localization of claim 1 wherein the specific targeting molecule comprises an antibody.

5. A macro-molecular complex for target localization comprising:
   an albumin central core having a surface thereof;
   a polysaccharide spacer arm coupled to the central core; and
   an antibody molecule coupled to the spacer arm; wherein the polysaccharide spacer arm comprises five monosaccharides to twenty-four thousand monosaccharides and wherein said polysaccharide is coupled to the surface of said central core such that said polysaccharide is not incorporated into said central core, said polysaccharide thereby being oriented so that the antibody molecule has translational freedom and reduced steric hindrance when coupled to the polysaccharide spacer arm.

6. The macro-molecular complex for target localization of claim 1 or 5 wherein the complex is labelled with a radiation producing substance.

7. The macro-molecular complex for target localization of claim 1 or 5 wherein the complex is labelled with a radioactive isotope.

8. The macro-molecular complex for target localization of claim 6 wherein the radioactive isotope comprises Tc-99m.

9. The macro-molecular complex for target localization of claim 5 wherein the complex is in lyophilized form.

10. A process for producing a macro-molecular complex with a central core coupled to a polysaccharide spacer arm that is coupled to a specific targeting molecule comprising:
    forming a bio-compatible central core suitable for in-vivo circulation;
    coupling a polysaccharide spacer arm to the central core; and
    coupling the spacer arm to a specific targeting molecule;

wherein the polysaccharide spacer arm comprises five monosaccharides to twenty-four thousand monosaccharides.

11. The process for producing a macro-molecular complex of claim 10 wherein the central core comprises albumin.

12. The process for producing a macro-molecular complex of claim 10 wherein the central core is treated to increase the number of carboxylic residues.

13. The process for producing a macro-molecular complex of claim 10 wherein the coupling of the polysaccharide spacer arm to the central core comprises:
   coupling hydrazine to terminal ends of the polysaccharide spacer arm; and
   coupling the hydrazine-coupled polysaccharide spacer arm to the central core.

14. The process for producing a macro-molecular complex of claim 10 wherein the coupling of the polysaccharide spacer arm to the central core comprises:
   coupling a dihydrazide to the polysaccharide spacer arm; and
   coupling the hydrazide-coupled polysaccharide spacer arm to the central core.

15. The process for producing a macro-molecular complex of claim 10 wherein the coupling of the polysaccharide spacer arm to the central core comprises:
   coupling a first dihydrazide to the central core;
   coupling a terminal end of the polysaccharide spacer arm to the dihydrazide coupled to the central core; and
   coupling a second dihydrazide to an uncoupled terminal end of the polysaccharide spacer arm.

16. The process for producing a macro-molecular complex of claim 10 wherein the polysaccharide spacer arm is dextran.

17. The process for producing a macro-molecular complex of claim 10 wherein the specific targeting molecule comprises an antibody.

18. The process for producing a complex of claim 10 further comprising labelling the complex with radioactive isotope.

19. A process for producing a macro-molecular complex with a central core coupled to a polysaccharide spacer arm that is coupled to a specific targeting molecular comprising:
   heat stabilizing albumin to form microspheric central cores suitable for in-vivo use;
   coupling a polysaccharide spacer arm to the albumin central core; and
   coupling the spacer arm to an antibody molecule;
   wherein the polysaccharide spacer arm comprises five monosaccharides to twenty-four thousand monosaccharides.

20. A macro-molecular complex for target localization produced by:
   forming a bio-compatible central core suitable for in-vivo circulation;
   coupling a polysaccharide spacer arm to the central core; and
   coupling the spacer arm to a specific targeting molecule; wherein said polysaccharide spacer arm comprises five monosaccharides to twenty-four thousand monosaccharides.

21. The macro-molecular complex for target localization of claim 20 wherein said central core comprises albumin, said polysaccharide spacer arm comprises dextran, and said specific targeting molecule comprises an antibody.

* * * * *

UNITED STATES PATENT AND TRADEMARK OFFICE
CERTIFICATE OF CORRECTION

PATENT NO. : 5,216,130

DATED : June 1, 1993

INVENTOR(S) : Bruce R. Line and Peter B. Weber

It is certified that error appears in the above-identified patent and that said Letters Patent is hereby corrected as shown below:

In claim 8, column 12, line 54, change "6" to --7--.

In claim 19, column 14, lines 12-13, change "molecular" to --molecule--.

Signed and Sealed this

Eighteenth Day of January, 1994

BRUCE LEHMAN

*Attest:*

*Attesting Officer*     *Commissioner of Patents and Trademarks*